(12) United States Patent
Black et al.

(10) Patent No.: US 7,363,821 B2
(45) Date of Patent: Apr. 29, 2008

(54) SYSTEMS AND METHODS FOR FATIGUE TESTING STENTS

(75) Inventors: Erin Black, Middlesex, NJ (US); Robert Burgermeister, Bridgewater, NJ (US); Randy-David Burce Grishaber, Asbury, NJ (US); David W. Overaker, Annandale, NJ (US)

(73) Assignee: Cordis Corporation, Miami Lakes, FL (US)

( * ) Notice: Subject to any disclaimer, the term of this patent is extended or adjusted under 35 U.S.C. 154(b) by 54 days.

(21) Appl. No.: 11/511,096

(22) Filed: Aug. 28, 2006

(65) Prior Publication Data

US 2008/0047356 A1    Feb. 28, 2008

(51) Int. Cl.
  *G01N 3/32* (2006.01)
(52) U.S. Cl. ........................................... 73/810
(58) Field of Classification Search ............ 73/810, 73/849; 623/17, 2.11
  See application file for complete search history.

(56) References Cited

U.S. PATENT DOCUMENTS

| | | | | |
|---|---|---|---|---|
| 4,972,721 A | * | 11/1990 | Conti | 73/807 |
| 5,575,764 A | * | 11/1996 | Van Dyne | 602/26 |
| 5,670,708 A | * | 9/1997 | Vilendrer | 73/37 |
| 5,683,465 A | * | 11/1997 | Shinn et al. | 623/17.14 |
| 5,893,889 A | * | 4/1999 | Harrington | 623/17.16 |
| 6,417,682 B1 | * | 7/2002 | Suzuki et al. | 324/755 |
| 6,810,751 B2 | * | 11/2004 | Moreno et al. | 73/849 |
| 6,881,224 B2 | * | 4/2005 | Kruse et al. | 623/2.11 |
| 7,254,988 B2 | * | 8/2007 | Keeble | 73/37 |
| 2004/0013997 A1 | * | 1/2004 | Jung et al. | 433/57 |

* cited by examiner

*Primary Examiner*—Michael Cygan
*Assistant Examiner*—Octavia Davis (57) ABSTRACT

Systems and methods for fatigue testing one or more stents based on measured electrical resistance levels of each stent. Pairs of lead lines from an ohmmeter are connected to a respective stent. The respective stent is mounted onto an expander having an interior tapered portion into which a correspondingly tapered expansion pin is received. Cyclic loading strains are applied to the respective stent as an expansion pin is inserted into a corresponding one of the expanders. Stent fracture or failure occurs when cyclic loading exceeds the stents architectural and material capacity. Such fracture fatigue or failure is identified by increased electrical resistance levels. Resistance may be continuously monitored to more readily identify the onset of fatigue or failure. The expansion pins extend from a movable plate, and the expanders comprise a part of corresponding stations that extend from a fixed plate.

19 Claims, 6 Drawing Sheets

SYSTEMS AND METHODS FOR FATIGUE TESTING STENTS

BACKGROUND OF THE INVENTION

1. Field of the Invention

The invention generally relates to systems and methods for fatigue testing one or more stents. More specifically, the invention relates to systems and methods for determining fatigue levels of one or more stents based on electrical resistance data associated with the one or more stents.

2. Related Art

Modern medical procedures routinely employ implants placed in a patient's vascular system to perform various therapeutic functions. As an example, stents are often inserted in an artery of a patient to maintain a flow lumen through the artery at a location that had previously been at least partially blocked. Ideally such stents, or other vascular prostheses, are able to withstand the physiological dynamics that occur within the vessel or organ in which they are emplaced. Where fracture, or other failure, of the stent, or other prosthesis, occurs removal and replacement thereof is typically necessitated. Providing a stent, or other prosthesis, of suitable strength and durability for implantation into a patient, to minimize the likelihood of failure and the associated removal and replacement thereof is thus desirable. Determining the approximate fatigue tendencies of the stent, or other prosthesis, helps accomplish the provision of a suitable stent, or other prosthesis.

Typical fatigue testers, such as in U.S. Pat. No. 4,972,721 to Conti, include motorized arrangements that drive bellows and pulse fluids into the lumen of a stent specimen to determine fatigue tendencies thereof. For example, U.S. Pat. No. 4,972,721 to Conti, discloses such an arrangement whereby fluid is pulsed or oscillated to simulate the physiological conditions the specimen would be subjected to when emplaced within the vasculature of a patient. A linear voltage-to-displacement transducer (LVDT) then measures the volume of fluid in each pulse provided by the bellows, whereas another LVDT transducer measures a change in length of the specimen during the pulsing. The suitableness of the specimen for the expected physiological parameters of a patient are then determined based on the obtained volume and length change information, which are used to calculate compliability and fatigue tendencies of a specimen based on changes in pressure, radius and length of the specimen. The number of cycles required for to render such arrangements reliable can prove cumbersome, however. Moreover, in fatigue testers where the specimen is positioned within a flexible tubing during testing, cyclic loading tends to be small. A need exists therefore for quick, easy and reliable systems and methods of determining fatigue tendencies of one or more stents by subjecting the one or more stents to larger cyclic loading strains under accelerated conditions.

SUMMARY OF THE INVENTION

The systems and methods of the invention provide a stent fatigue tester for one or more stents. The fatigue tester is comprised of a lower plate, an upper plate, a series of stations extending upwardly from one of the lower plate and the upper plate, and a corresponding series of expansion pins extending downwardly from the other of the upper plate and the lower plate. One of the lower plate and the upper plate is fixed, whereas the other of the lower plate and the upper plate is movable relative to the fixed plate.

Each expansion pin is tapered to narrow as it extends from the plate associated therewith. Each station is further comprised of an adjuster, a portion of which is threadably received in a passage of the lower plate. A tubular C-shaped expander extends therefrom each adjuster. Each C-shaped expander further comprises a tapered interior that corresponds to the taper of a respective expansion pin that will be received therein. Each C-shaped expander is thus also generally coaxially aligned with a corresponding expansion pin of the upper plate for receipt thereof. Each tapered C-shaped expander thus receives the correspondingly tapered expansion pin when the upper plate and lower plate are closed towards one another during testing.

Each station further comprises an adjuster and a retainer secured thereto. Each adjuster further comprises a threaded hub to which a respective retainer is secured. The retainer thus helps secure the expander relative to the adjuster. Guide pins are provided on one of the upper plate or lower plate in order to help align the expansion pins with the corresponding expanders when the upper plate and the lower plate are closed toward one another for testing.

A respective one of the one or more stents is arranged over a corresponding expander for testing thereof. Each stent is provided with wire leads connecting the respective stent to an ohmmeter. Electrical resistance of each stent is thereafter monitored by the ohmmeter as cyclic strains are imparted to the respective one or more stents by insertion of the respective expansion pins into the corresponding expanders occurs. Relatively large cyclic strains are imparted to the stents, as compared to conventional fatigue testers using internal pressurization of tubing into which a stent has been deployed. When the number of strain cycles exceeds the fatigue limit of the stent, resulting in fracture or other architectural failure of the stent, a change in resistance is identified by the ohmmeter. An increase in resistance typically identifies a failure or other compromise in the one or more struts. The onset of fatigue or failure is more readily monitored and identified than in conventional fatigue testers. Furthermore, the ability to impose relatively larger cyclic strains enables an accelerated fatigue test in which the same mode of failure can be achieved in fewer cycles, and therefore in shorter time. Stents of different designs, materials, or structural configurations are more readily compared according to the systems and methods described herein, as well.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 1:
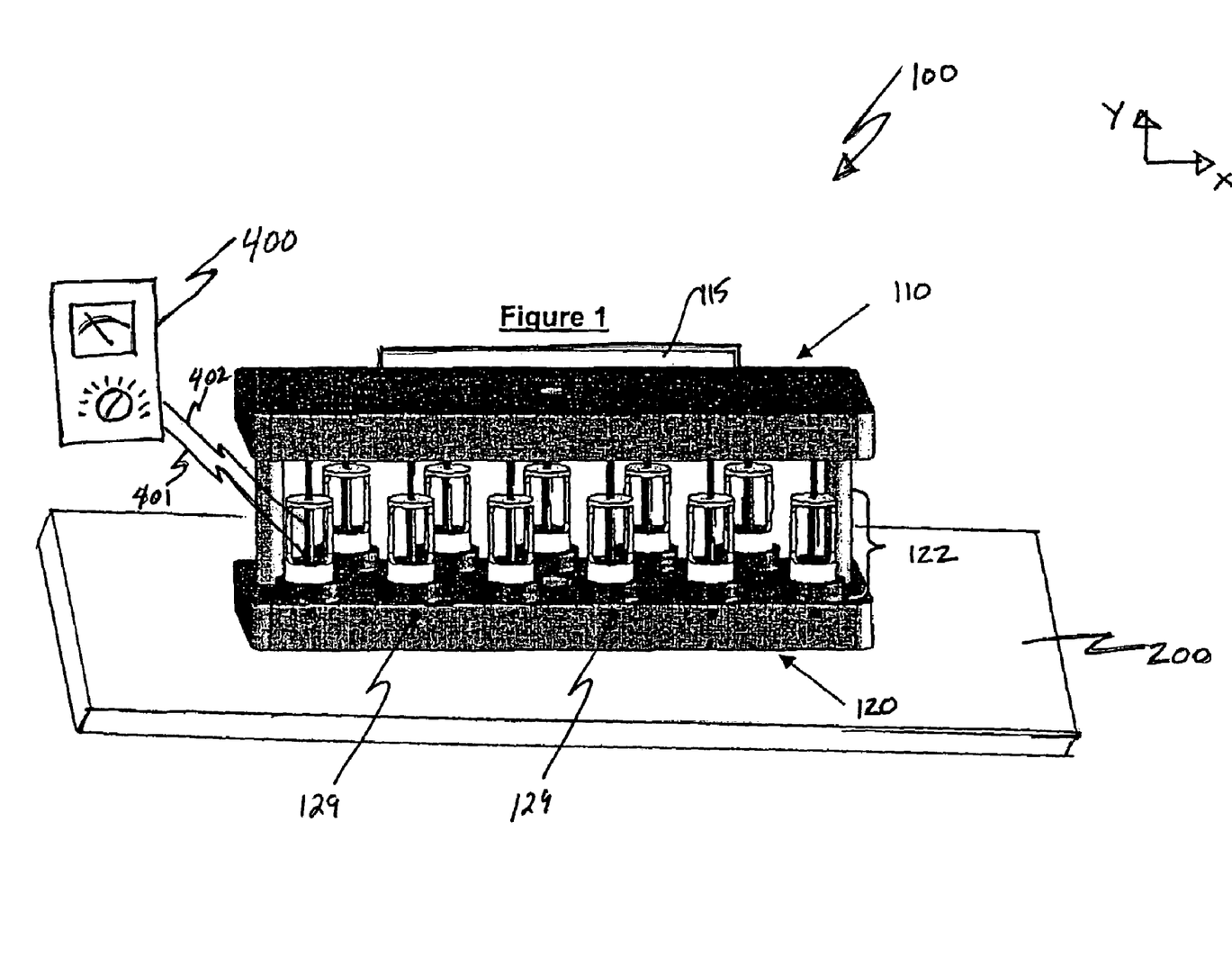
FIG. 1 illustrates a schematic view of an embodiment of a stent fatigue tester according to the systems and methods of the invention.

FIG. 1 illustrates schematically an embodiment of a stent fatigue tester 100 according to the systems and methods of the invention. The stent fatigue tester 100 comprises an upper plate 110 and a lower plate 120. As shown in FIG. 1, the lower plate 120 is fixedly connected to a table top 200, a load cell or other structure, for example, and the upper plate 110 is movable relative to the fixed lower plate 120. The upper plate 110 may be attached to a crosshead 115, or other structure, to accommodate the movement thereof the upper plate. Of course, although not shown, the artisan will readily appreciate that the inverse is also achievable within the context of the fatigue tester 100 described herein such that the upper plate 110 is fixed and the lower plate 120 is movable relative thereto. In any event, the movable plate is movable in the X and Y directions in order to better align the fixed plate with one another in operation. Although omitted from subsequent views, the table top 200, load cell or other structure, to which the lower plate is fixed, is understood to be a part of the stent fatigue tester 100, as otherwise described herein.

Figure 2:
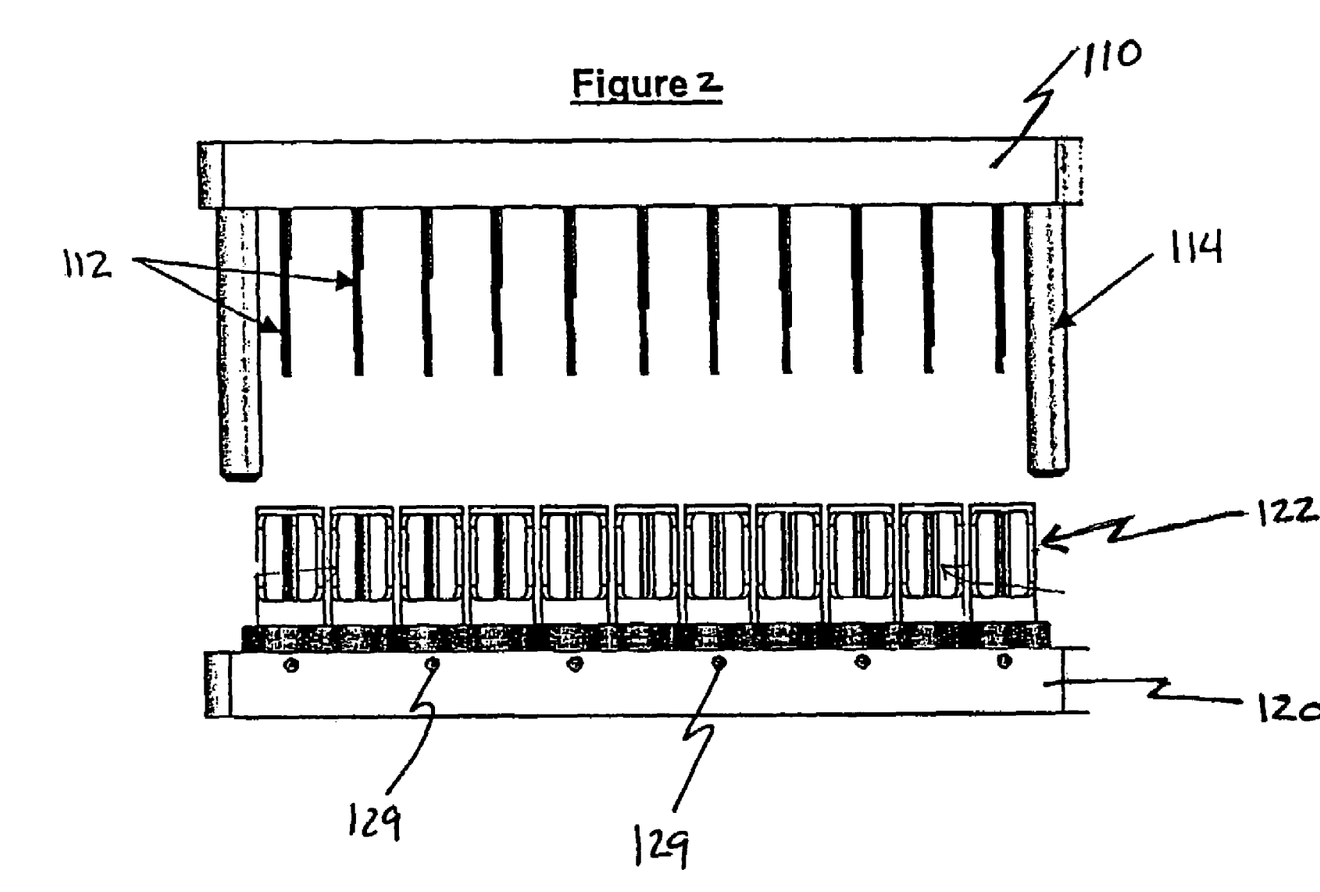
FIG. 2 illustrates a schematic view of the stent fatigue tester of FIG. 1 in an open position according to the invention.
Figure 3:
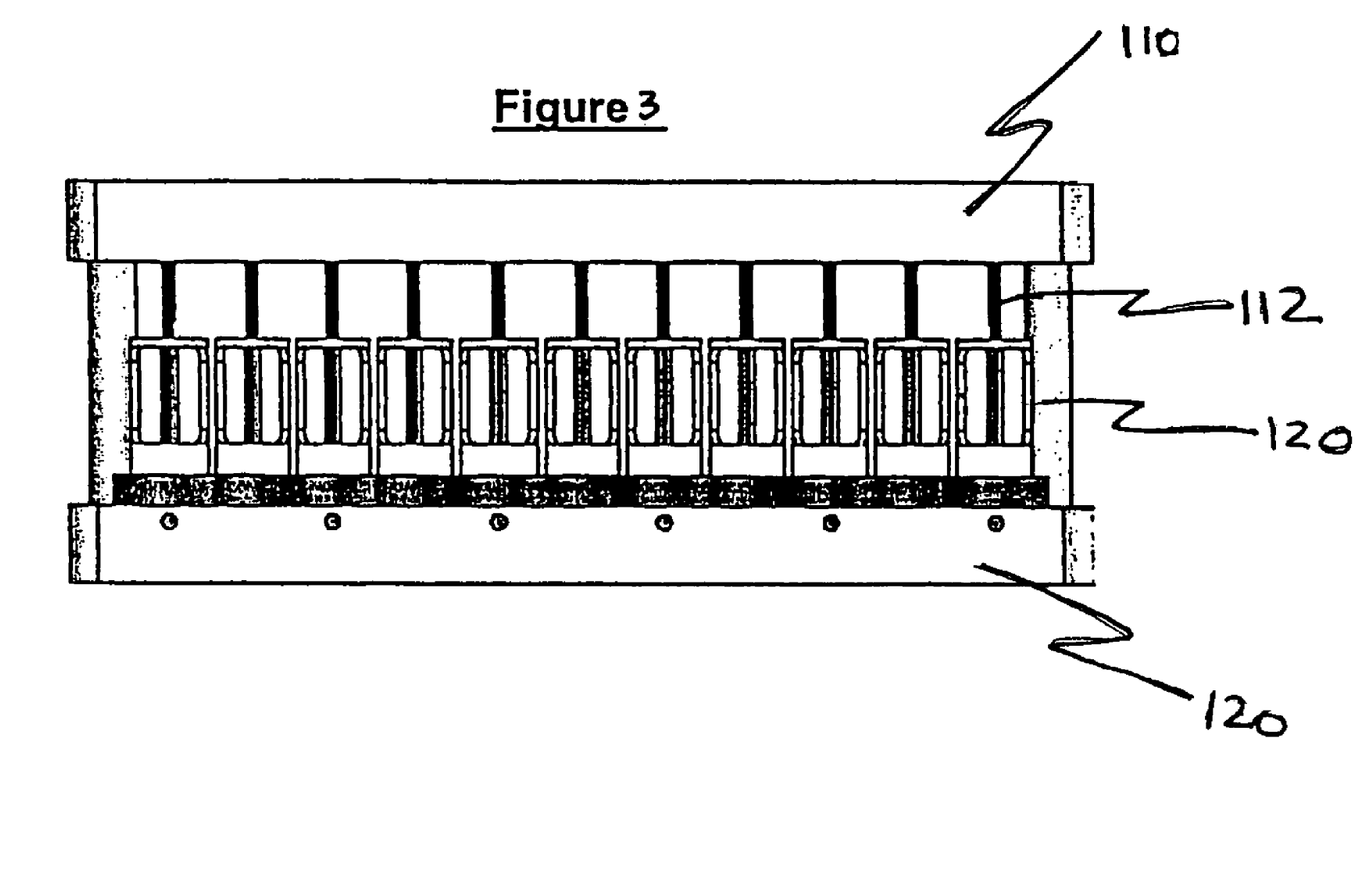
FIG. 3 illustrates a schematic view of the stent fatigue tester of FIGS. 1-2 in a closed testing position according to the invention.

Referring to FIGS. 1-3, the stent fatigue tester 100 further comprises a series of tapered expansion pins 112 extending downwardly from the upper plate 110, and a series of expansion pin receiving stations 122 extending upwardly from the lower plate 120, the stations 122 corresponding to a respective one of the expansion pins 112. FIG. 2 most clearly shows the expansion pins 112 of the upper plate 110 and the stations 122 of the lower plate 120 with the upper and lower plates in an open, i.e., dis-engaged, position relative to one another. Also shown in FIG. 2 are guide pins 114 extending downwardly from opposite ends of the upper plate 110. The guide pins 114 extend slightly further downwardly than the expansion pins 112 from the upper plate 110 and help to align the expansion pins 112 with the stations 120 of the lower plate 120. FIG. 3 illustrates the upper and lower plates in a closed, i.e., engaged, position such that the tapered expansion pins 112 are received in a corresponding one of the stations 122.

FIG. 1 illustrates a series of eleven stations 120 and corresponding expansion pins 112 arranged in a staggered row configuration along the respective upper and lower plates. Although the staggered row configuration is preferable to aid visual inspection and optical measurement of the stents tested therein, the artisan will appreciate that other arrangements and configurations of stations and expansion pins are within the realm of the stent fatigue tester described herein, provided a respective station corresponds to a respective expansion pin. Different quantities or linear arrangements and configurations of the expansion pins and corresponding stations are thus contemplated as comprising the various embodiments of the stent fatigue tester described herein. The artisan will also readily appreciate that, although not shown, the expansion pins could instead extend upwardly from the lower plate and the stations could extend downwardly from the upper plate, or some combination thereof could be provided, so long as the tapered expansion pins and stations are configured to correspond with one another when the upper and lower plates assume the closed, i.e., engaged, position. The artisan will still further appreciate that the guide pins could instead be provided to extend upwardly from the lower plate, could instead be provided at locations other than the ends of the respective upper or lower plates, or could be provided in some combination of the above so long as the guide pins are configured to help align the expansion pins with a corresponding station according to the various embodiments of the stent fatigue tester otherwise described herein.

Figure 4:
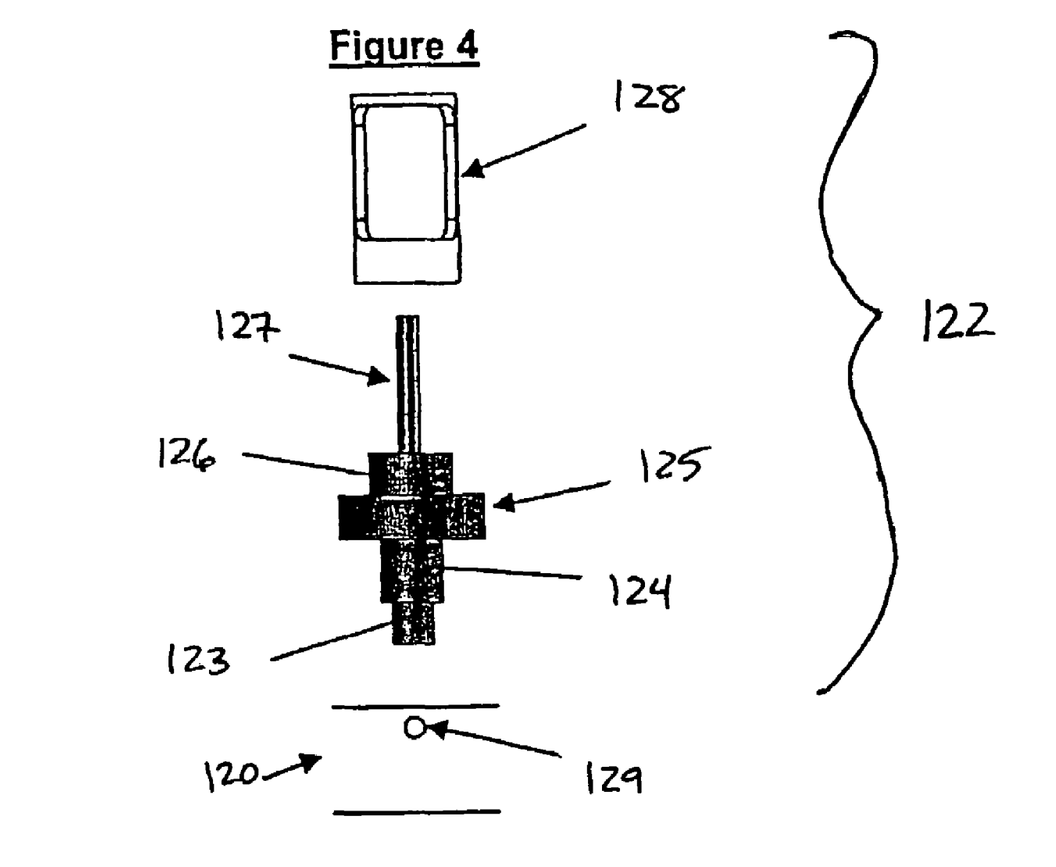
FIG. 4 illustrates an exploded view of a station of the stent fatigue tester of FIGS. 1-3 according to the invention.

FIG. 4 illustrates an exploded view of an exemplary station 122 according to the stent fatigue tester 100 shown in FIGS. 1-3, for example. The station 122 comprises a threaded post 123 at one end and a C-shaped expander 127 at an opposite end. The threaded post 123 threadably engages a lower passage 121a (FIGS. 6 and 7) provided in the lower plate 120, which help secure the station 122 to the lower plate 120. A smooth hub 124, circumferentially larger than the threaded post 123, is received within a non-threaded upper passage 121b (FIG. 6) of the lower plate. An axially centralized adjuster 125, circumferentially larger than the smooth hub 124, extends from the smooth hub 124 and seats along an upper surface of the lower plate 120 when the threaded post 123 of the station 122 is fully received within the threaded lower passage. A set screw 129 is provided through a portion of the lower plate 120, which set screw 129 contacts the smooth hub 124 to help lock the adjuster 125 relative to the lower plate.

Referring still to FIG. 4, a threaded hub 126, circumferentially smaller than the adjuster 125, extends upwardly from the adjuster 125, and the C-shaped expander 127 extends upwardly therefrom the threaded hub 126. The C-shaped expander 127 includes an interior portion that is tapered to correspond with the taper of a corresponding one of the expansion pins 112 of the upper plate 110, while the open-slit provided by the C-shape of the expander enables a respective one of the increasingly larger tapered expansion pin 112 to be received therein. Cyclic translation of an expansion pin 112 into a respective expander 127 thus produces cyclic diametral expansion of the expander 127 that is imparted to a stent 300 (FIG. 7) placed thereon.

Ideally, the expander 127 is comprised of a stiff plastic so that compressive deformation of the expander 127 between the stent 300 and the respective expansion pin 112 is minimized. In this manner, the diametral changes of the expander 127 are more directly transmitted to the stent 300. Preferably, also, the dynamic coefficient of friction between the tapered expander 127 and the tapered expansion pin 112 is low in order to minimize wear otherwise generated by the cyclic loading.

Also shown in FIG. 4, each station further comprises a retainer 128. The retainer 128 is threadably secured to the threaded hub 126 of the station 122. The retainer 128 thus helps secure the position of the expander 127 relative to the adjuster 125.

Figure 5:
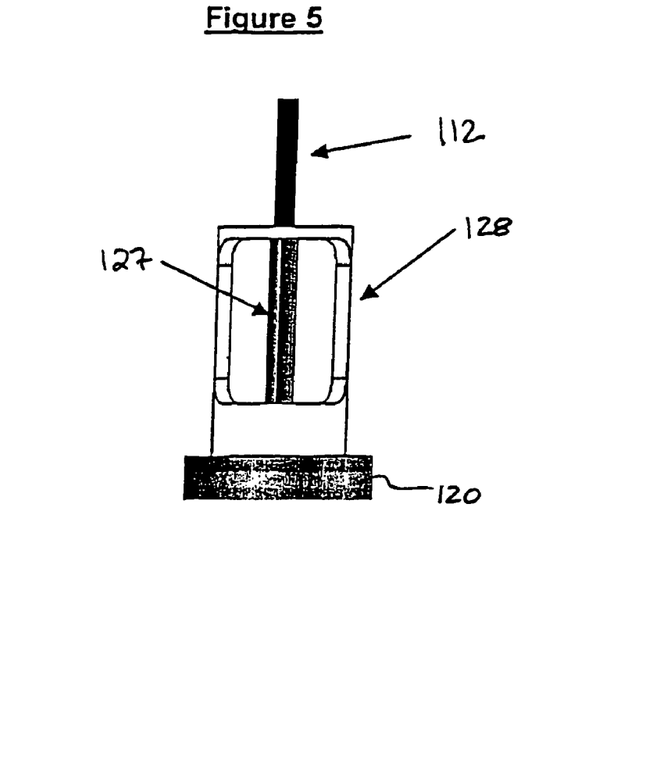
FIG. 5 illustrates a detail view of a station with an expansion pin passing through a station of the stent fatigue tester of FIGS. 1-4 according to the invention.
Figure 6:
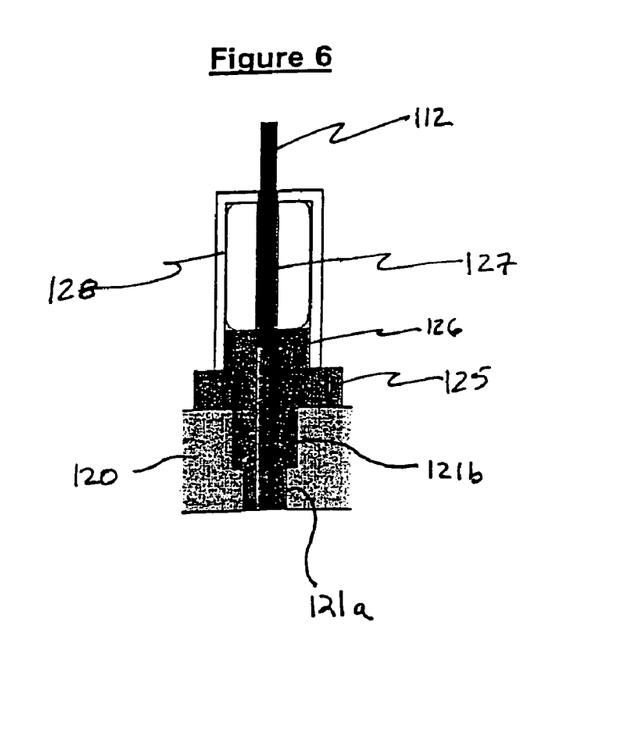
FIG. 6 illustrates a cross sectional view of a station with an expansion pin passing through a station of the stent fatigue tester of FIGS. 1-4 according to the invention.

FIG. 5 illustrates a detail view of the station 122 of FIG. 4, for example, wherein one of the tapered expansion pins 112 is inserted into the correspondingly tapered C-shaped expander 127 of a station 122. FIG. 6 illustrates a cross-sectional view of the same.

Figure 7:
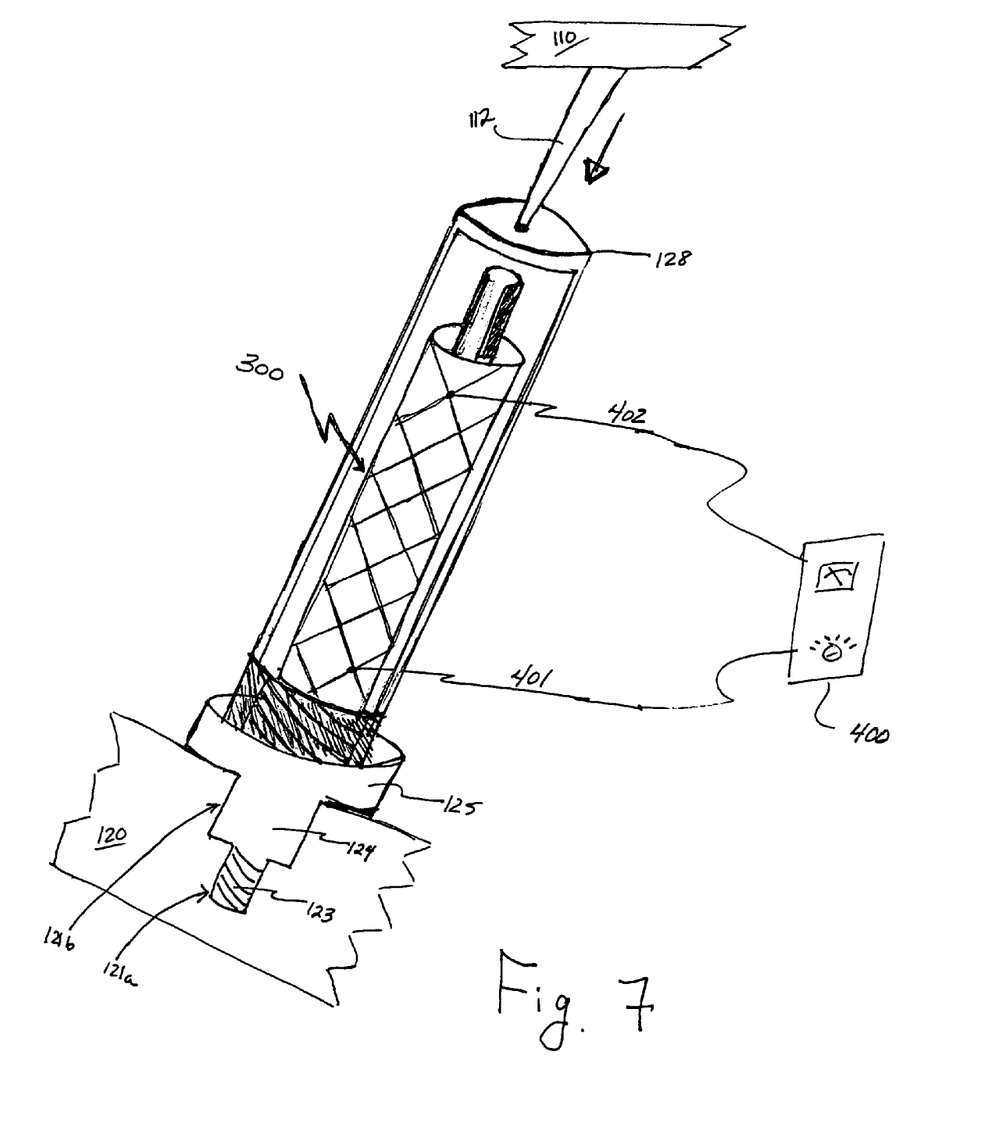
FIG. 7 illustrates a stent with wire leads extending therefrom for connection to an ohmmeter of the stent fatigue tester of FIGS. 1-4 according to the invention.

Referring to FIG. 7, a stent 300 is placed over an expander 127 prior to insertion of the corresponding expansion pin 112 for fatigue testing thereof. An ohmmeter 400 (FIG. 1) is connected to each stent 300 by respective pairs of lead lines 401, 402 (FIGS. 1 and 7). The electrical resistance of each stent is thus monitored by the ohmmeter 400 as the expansion pins 112 are inserted into the expander 127 of a respective station 122. In this way, the fatigue or failure load of a stent 300 is readily identified when the ohmmeter 400 detects a rapid rise in electrical resistance of the stent.

In practice, as shown in FIGS. 1-7, the upper plate 110 and lower plate 120 are arranged in the open position relative to one another, and one or more stents 300 is placed over one or more of the C-shaped expanders 127 (only one shown in FIGS. 6 and 7). The stents 300 may comprise the same design, different designs, or combinations thereof. Pairs of lead lines 401, 402 from an ohmmeter 400 (FIGS. 1 and 7) are attached to each stent 300 and a baseline electrical resistance level for each stent 300 is determined. The upper plate 110 is then moved relative to the fixed lower plate 120 so as to insert respective tapered expansion pins 112 into a corresponding one of the tapered C-shaped expanders 127 of the stations 122. As the expansion pins 112 are inserted further into the corresponding expanders 127 the diameter of the expander increases and is imparted to the respective stent 300 positioned thereon. Resistance levels of the respective stents 300 are monitored and measured by the ohmmeter and stored in a database. The data of measured resistance levels may be networked into a live graphical display, if desired, for easy display and access throughout a test. In this manner, the initiation of failure or other compromise of a stent may be more readily identified.

When the cyclic loads imparted to a stent by insertion of the respective expansion pin 112 into a corresponding expander 127 exceed that stent's architectural and material capacity, than a fracture or other compromise of the stent 300 occurs. An increased electrical resistance level is identified by the ohmmeter 400. Failed or compromised stents may be visually inspected, discarded and replaced, if desired. Large cyclic loads are thus imparted to the stents and fatigue information about the stents is readily determinable under accelerated conditions as a result. Individual stents are readily monitored in this manner to determine their fatigue or failure tendencies under large cyclic loads. Multiple stents are also readily monitored using a multi-channel ohmmeter whereby each stent 300 is assigned to a designated channel.

Preferably, the wire leads 401, 402 are connected to ends of the respective stent 300. The wire leads 401, 402 may be connected using laser welding techniques, soldering, arc welding and conductive epoxies, for example, or any other conventional manner known in the art.

The various exemplary embodiments of the invention as described hereinabove do not limit different embodiments of the present invention. For example, the various components comprising the stent fatigue tester described herein may be secured to the respective upper and lower plates other than as shown or described herein without departing from the scope and breadth of the stent fatigue tester and method set forth. Further, the materials described herein are not limited to the materials, designs, or shapes referenced herein for illustrative purposes only, and may comprise various other materials, designs or shapes suitable for the systems and procedures described herein as should be appreciated by one of ordinary skill in the art.

In addition to the stent fatigue tester and method described herein, the one or more stents being tested may be fitted into a flexible tubing sleeve during test so as to simulate the physiological constraints a stent would incur when emplaced within the anatomy of a subject patient. The flexible tubing sleeve would preferably be comprised of materials with properties approximating the properties of a human vessel, or other duct or organ, for example.

Still further, the stent fatigue tester could be placed in an environmental chamber to more closely approximate, during testing, the physiological conditions the stent would likely incur when emplaced within a vessel, duct or other organ of a patient.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A stent fatigue tester comprising:
   a fixed plate;
   a movable plate;
   a series of tapered expansion pins extending from the movable plate;
   a series of stations extending from the fixed plate, each station having a tapered expander over which a respective stent is placed and for receipt of a corresponding one of the tapered expansion pins; and
   lead lines connecting each stent to an ohmmeter for determining electrical resistance of the stent as the respective expansion pins are cyclically inserted into a corresponding one of the expanders.

2. The stent fatigue tester of claim 1, wherein each station further comprises:
   a threaded post;
   a smooth hub;
   an adjuster;
   a threaded hub, the expander extending from the threaded hub for receipt of a respective one of the expansion pins; and
   a retainer.

3. The stent fatigue tester of claim 2, wherein the fixed plate further comprises a threaded passage into which the threaded post of the station is received.

4. The stent fatigue tester of claim 3, wherein the fixed plate further comprises a non-threaded passage into which the smooth hub is received.

5. The stent fatigue tester of claim 4, further comprising a set screw penetrating through the fixed plate and against a portion of the smooth hub to secure the adjuster relative to the fixed plate.

6. The stent fatigue tester of claim 1, further comprising guide pins extending from one of the fixed or movable plates to help align the expansion pins with the corresponding expanders.

7. The stent fatigue tester of claim 5, wherein the retainer is threadably secured to the threaded hub to help secure the expander relative to the adjuster.

8. The stent fatigue tester of claim 7, wherein the expansion pins and the stations are arranged in staggered rows on the respective fixed and movable plates.

9. The stent fatigue tester of claim 7, wherein expander is comprised of materials configured to minimize compressive deformation between the stent mounted thereon and the respective expansion pin inserted therein.

10. The stent fatigue tester of claim 9, wherein the expander is comprised of plastic.

11. The stent fatigue tester of claim 1, wherein the lead lines are connected to a respective stent by any of laser welding, soldering, arc welding, and conductive epoxies.

12. The stent fatigue tester of claim 1, further comprising one or more stents mounted individually on a respective expander of a respective station from among the series of stations for testing thereof based on electrical resistance levels measured by the ohmmeter.

13. The stent fatigue tester of claim 12, wherein the one or more stents is comprised of stents having a common design.

14. The stent fatigue tester of claim 13, wherein the stents are comprised of a common material.

15. The stent fatigue tester of claim 13, wherein the stents are comprised of different materials.

16. The stent fatigue tester of claim 12, wherein the one or more stents is comprised of stents having different designs.

17. The stent fatigue tester of claim 16, wherein the stents are comprised of a common material.

18. The stent fatigue tester of claim 16, wherein the stents are comprised of different materials.

19. The stent fatigue tester of claim 1, further comprising a graphical monitor networked with the ohmmeter and configured to display resistance levels of one or more stents mounted on the expander and subjected to cyclic loading by insertion of a respective expansion pin into the corresponding expander to determine failure or fatigue of the one or more stents.

* * * * *